United States Patent
Engel et al.

(10) Patent No.: US 7,288,517 B2
(45) Date of Patent: Oct. 30, 2007

(54) TREATMENT OF DEMENTIA AND NEURODEGENERATIVE DISEASES WITH INTERMEDIATE DOSES OF LHRH ANTAGONISTS

(75) Inventors: Jürgen Engel, Alzenau (DE); Rainer Voegeli, Biebergemünd-Bieber (DE)

(73) Assignee: AEterna Zentaris GmbH, Frankfurt (DE)

( * ) Notice: Subject to any disclaimer, the term of this patent is extended or adjusted under 35 U.S.C. 154(b) by 132 days.

(21) Appl. No.: 10/133,967

(22) Filed: Apr. 27, 2002

(65) Prior Publication Data

US 2002/0177556 A1 Nov. 28, 2002

Related U.S. Application Data

(60) Provisional application No. 60/287,434, filed on Apr. 30, 2001.

(51) Int. Cl.
*A01N 37/18* (2006.01)
*A61K 38/00* (2006.01)

(52) U.S. Cl. .......................................... 514/2; 514/800

(58) Field of Classification Search ................... 514/2; 530/300
See application file for complete search history.

(56) References Cited

U.S. PATENT DOCUMENTS 3,135,743 A 6/1964 Clinton

FOREIGN PATENT DOCUMENTS

| CA | 2309395 | 12/2000 |
|---|---|---|
| EP | 1393747 A1 | 3/2004 |
| WO | WO97/44339 | 11/1997 |
| WO | WO 00/55190 | 9/2000 |
| WO | WO 00/69859 | 11/2000 |
| WO | WO 01/29044 A1 | 4/2001 |
| WO | WO 01/78780 A1 | 10/2001 |
| WO | WO 02/02533 A1 | 1/2002 |

OTHER PUBLICATIONS

Reissmann T, et al. Human Reproduction Update 6(4):322-331, 2000.*
Herausgegeben von Lothar Thomas, Labor und Diagnose, 5. Erweiterte Auflage 2000, Seite 44, 44.2.5.
Serono Europe Limited, Catrotide, Apr. 13, 1999.
Eda: N. N. Yakhno, D. R. Shtulman, P. Y. Melnitchuk, E. M. Burtsev, "The diseases of Nervous System", Zhumal Nevrologil I Palkhiatril, Maditsina Moscow 1996, pp. 114-124.
Kiyofumi Yamada and Toshitaka Nabeshima. "Animal models of Alzheimer's disease and evaluation of anti-demenile drugs," Pharmacology & Therapeutics 88, 93-113 (2000).
Christine Sturchler-Pierrat and Bernd Sommer. "Transgenic Animals in Alzheimer's Disease Research," Reviews in the Neurosciences, 10, 15-24 (1999).

* cited by examiner

*Primary Examiner*—Robert S. Landsman
(74) *Attorney, Agent, or Firm*—Goodwin Procter LLP

(57) ABSTRACT

The present invention relates to the treatment of dementia and neurodegenerative diseases like Alzheimer's disease with intermediate doses of LHRH antagonists which do not cause a castration. A preferred LHRH antagonist is cetrorelix.

14 Claims, No Drawings

TREATMENT OF DEMENTIA AND NEURODEGENERATIVE DISEASES WITH INTERMEDIATE DOSES OF LHRH ANTAGONISTS

This application claims the benefit of U.S. Provisional Application No. 60/287,434 filed on Apr. 30, 2001.

FIELD OF INVENTION

The present invention relates to the treatment of dementia and neurodegenerative diseases.

BACKGROUND OF THE INVENTION

Furuya, Shuichi et al. teach preventives and remedies for Alzheimer's disease containing a GnRH antagonist for preventing and treating Alzheimer's disease with little toxicity in WO 01/78780.

SUMMARY OF THE INVENTION

The present invention relates to the treatment of dementia and neurodegenerative diseases with an effective dose of LHRH antagonists.

DETAILED DESCRIPTION OF THE INVENTION

It has been shown in a study by Bowen R. L et al. that serum concentrations of follicle-stimulating hormone (FSH) and luteinizing hormone (LH) were significantly higher in individuals suffering from dementia, e.g. Alzheimer's disease. Bowen R. L. et al. proposed to lower FSH and LH to minimal levels by the use of high doses of LH-releasing hormone (LHRH) analogues which are either super-agonists or antagonists (CA U.S. Pat. No. 2,309,395, priority Jun. 4, 1999, Ser. No. 09/326,180) of LHRH. This treatment would be accompanied by highly undesirable side effects such as the lowering of sex hormone levels to levels that result in chemical castration, e.g., loss or reduction of libido, sexual desire and sexual potency. In men and pre-menopausal women this treatment would also result in the typical symptoms of decreased levels of sex hormones such as hot flashes, etc. Women would additionally suffer from loss of bone minerals that would limit the usefulness of the treatment. These side effects could be reduced by hormone replacement therapy.

It has now been discovered that treatment with intermediate doses of LHRH antagonists will result in a submaximal lowering of FSH and LH levels to normal levels that leave sex hormone levels above the chemical castration threshold. This treatment is highly advantageous as it gives the desired results of normalizing FSH and LH levels without the undesirable side-effects of sex hormone inhibition. Thus the additional treatment with sex hormone replacement therapy becomes superfluous.

The present invention relates to the treatment of dementia and neurodegenerative diseases with intermediate doses of LHRH antagonists, wherein the antagonist is preferably cetrorelix, teverelix, antide or abarelix. The antagonist can also be the LHRH antagonist D-63 153 (Ac-D-Nal-D-p-Cl-Phe-D-Pal-Ser-N-Me-Tyr-D-Hci-Nle-Arg-Pro-D-Ala-NH$_2$) as described in the PCT application WO 00/55190 A1, where Nal is 2-napthylalanine, p-Cl-Phe is p-chlorophenylalanine, Pal is 3-pyridylalanine, Hci is homocitrulline and Nle is norleucine.

The mentioned LHRH antagonists can also exhibit a heterocyclic skeletal structure. Such peptidomimetics can be for example:
- 1-[7-Chloro-3-(3,5-dimethyl-phenyl)-2-oxo-4-(2-piperidin-2-yl-ethoxy)-1,2-dihydro-quinolin-6-yl]-3-pyridin-2-yl-urea (described in WO 97/44339),
- 3-[Benzyl-methyl-amino)-methyl]-2-tert-butyl-8-(2-fluoro-benzyl)-6-(3-methoxy-phenyl)-7-methyl-8H-imidazo[1,2-a]pyrimidin-5-one (described in WO 01/29044),
- 2-(2,5-Dimethyl-furan-3-yl)-8-(2-fluoro-benzyl)-3-([methyl-(2-pyridin-2-yl-ethyl)-amino]-methyl)-5-oxo-5,8-dihydro-imidazo[1,2-a]pyrimidine-6-carboxylic acid 1-ethyl-propylester (described in WO 00/69859),
- 3-((2-[2-(3,5-Difluoro-phenyl)-1-(2-methoxy-benzoyl)-2-oxo-ethylidene]-2,3-dihydro-1H-benzoimidazol-5-yl-amino)-methyl)-benzonitrile (described in WO 02/02533).

An effective dose of the LHRH antagonist is given in a monthly dose of 10 to 100 mg and the treatment is administered for one month, two months or for several months. An effective dose is defined herein as a dose that is sufficiently limited as to not cause chemical castration.

In a preferred embodiment the LHRH antagonist is given in a monthly dose of 30 to 60 mg and the treatment is administered for one month, two months or for several months.

Pharmaceutical formulations of the LHRH antagonist suitable for the therapeutic management of dementia and neurodegenerative diseases may be for example:
a) acetate salt formulations of the active compounds in concentrations of 1 mg/1 mL or lower where the lyophilized powder may be dissolved in water or in gluconic acid for injection;
b) acetate salt formulations of the active compounds in concentration of 1.5 mg/1 mL to 5.0 mg/1 mL, preferably 2.5 mg/1 mL, where the lyophilized powder may be dissolved in water or in gluconic acid for injection;
c) pamoate salt formulations of the active compounds in concentrations of 10 mg/1 mL to 30 mg/1 mL, preferably 15 mg/1 mL, where the lyophilized powder may be dissolved in water or in gluconic acid for injection.

Suitable excipients and dosage forms are, for example, described by K. H. Bauer, K. -H. Frömming and C. Führer, Lehrbuch der Pharmazeutischen Technologie, $6^{th}$ edition, Stuttgart 1999, pages 163-186 (excipients) and pages 227-386 (dosage forms). This publication, including the references as cited therein, are hereby incorporated by reference.

The LHRH antagonist can be administered via subcutaneous, oral, intramuscular or inhalative routes.

EXAMPLE

The disease as mentioned may be treated in accordance with the following example. A single dose of 30-60 mg per month of cetrorelix is administered by injection. The treatment is administered once a month. In another embodiment the treatment is continued for two months or lasts several months after the administration of the single dose.

We claim:

1. A method of treatinig Alzheimer's disease in humans comprising the administration of an LHRH antagonist at a monthly dose of about 60 mg to about 100 mg to an Alzheimer's disease patient, wherein said monthly dose is administered as a single dose, and wherein said LHRH antagonist is selected from the group consisting of cetrorelix, teverelix, antide, abarelix, D-63153 and peptidomimetics, wherein said peptidomimetic is selected from the group consisting of:
- 1-[7-Chloro-3-(3,5-dimethyl-phenyl)-2-oxo-4-(2-piperidin-2-yl-ethoxy)-1,2-dihydro-quinolin-6-yl]-3-pyridin-2-yl-urea;
- 3-[Benzyl-methyl-amino)-methyl]-2-tert-butyl-8-(2-fluoro-benzyl)-6-(3-methoxyphenyl)-7-methyl-8H-imidazo[1,2-a]pyrimidin-5-one;
- 2-(2,5-Dimethyl-furan-3-yl)-8-(2-fluoro-benzyl)-3-([methyl-(2-pyridin-2-yl-ethyl)-amino]-methyl)-5-oxo-5,8-dihydro-imidazo[1,2-a]pyrimidine-6-carboxylic acid 1-ethyl-propylester; and
- 3-((2-[2-(3,5-Difluoro-phenyl)-1-(2-methoxy-benzoyl)-2-oxo-ethylidene]-2,3-dihydro-1H-benzoimidazol-5-yl-amino)-methyl)-benzonitrile.

2. The method of claim 1, wherein said monthly dose is about 60 mg.

3. The method of claim 1, wherein the administration Is continued for a month, two months or several months.

4. The method of claim 1, wherein said monthly dose is administered as a single dose.

5. The method of claim 1, wherein the treatment leaves sex hormone levels in the human receiving the treatment above the chemical castration threshold.

6. A method of treating Alzheimer's disease in humans comprising administration to a human in need thereof a single dose of about 60mg of cetrorelix per month.

7. The method of claim 6, wherein the treatment is continued for two or more months.

8. The method of claim 1, wherein said LHRH antagonist is cetrorelix.

9. The method of claim 1, wherein the LHRH antagonist is D-63153.

10. The method of claim 1, wherein said monthly dose is about 100 mg.

11. A method of treating Alzheimer's disease in humans comprising administering to a human need thereof a single dose of about 100mg of D-63153 per month.

12. The method of claim 11 wherein treatment is continued for two or more months.

13. A method of treating Alzheimer's disease in humans comprising administering to a human in need thereof a single dose of about 60mg of D-63153 per month.

14. A method of treating Alzheimer's disease in humans comprising the administration of an LHRH antagonist at a monthly dose of about 30 mg to about 100 mg to an Alzheimer's disease patient, wherein said monthly dose is administered as a single dose, and wherein said LHRH antagonist is selected from the group consisting of cetrorelix, teverelix, antide, abarelix, D-63153 and peptidomimetics, wherein said peptidomimetics is selected from the group consisting of:
- 1-[7-Chloro-3-(3,5-dimethyl-phenyl)-2-oxo-4-(2-piperidin-2-yl-ethoxy)-1,2-dihydro-quinolin-6-yl]-3-pyridin-2-yl-urea;
- 3-[Benzyl-methyl-amino)-methyl]-2-tert-butyl-8-(2-fluoro-benzyl)-6-(3-methoxyphenyl)-7-methyl-8H-imidazo[1,2-a]pyrimidin-5-one;
- 2-(2,5-Dimethyl-furan-3-yl)-8-(2-fluoro-benzyl)-3-([methyl-(2-pyridin-2-yl-ethyl)-amino]-methyl)-5-oxo-5,8-dihydro-imidazo[1,2-a]pyrimidine-6-carboxylic acid 1-ethyl-propylester; and
- 3-((2-[2-(3,5-Difluoro-phenyl)-1-(2-methoxy-benzoyl)-2-oxo-ethylidene]-2,3-dihydro-1H-benzoimidazol-5-yl-amino)-methyl)-benzonitrile.

* * * * *